(12) United States Patent
Snyder et al.

(10) Patent No.: US 12,303,311 B2
(45) Date of Patent: May 20, 2025

(54) SPECTRAL X-RAY IMAGING USING VARIABLE HIGH VOLTAGE X-RAY SOURCE

(71) Applicant: Teledyne DALSA B.V., Eindhoven (NL)

(72) Inventors: Jonathan E. Snyder, Park City, UT (US); Andriy A. Lomako, Waterloo (CA)

(73) Assignee: TELEDYNE DALSA B.V., Eindhoven (NL)

( * ) Notice: Subject to any disclaimer, the term of this patent is extended or adjusted under 35 U.S.C. 154(b) by 233 days.

(21) Appl. No.: 17/891,971

(22) Filed: Aug. 19, 2022

(65) Prior Publication Data

US 2023/0058177 A1  Feb. 23, 2023

Related U.S. Application Data

(60) Provisional application No. 63/279,371, filed on Nov. 15, 2021, provisional application No. 63/235,947, filed on Aug. 23, 2021.

(51) Int. Cl.
*A61B 6/00* (2024.01)
*A61B 6/03* (2006.01)
(Continued)

(52) U.S. Cl.
CPC .............. *A61B 6/482* (2013.01); *A61B 6/035* (2013.01); *A61B 6/4007* (2013.01);
(Continued)

(58) Field of Classification Search
CPC ....... A61B 6/482; A61B 6/035; A61B 6/4007; A61B 6/4042; A61B 6/4241;
(Continued)

(56) References Cited

U.S. PATENT DOCUMENTS 3,965,358 A     6/1976  Macovski
6,781,330 B1 *  8/2004  Koenck ............... H05H 7/02
                                              315/505
(Continued)

FOREIGN PATENT DOCUMENTS

AU    2013222295     *  8/2013  ............. G01T 1/29
AU    2013222295 B2 *  3/2015  ............ B82Y 30/00
(Continued)

*Primary Examiner* — Edwin C Gunberg
*Assistant Examiner* — Richard O Toohey
(74) *Attorney, Agent, or Firm* — Snell & Wilmer LLP

(57) ABSTRACT

Methods, systems, and apparatus for performing spectral tomographic reconstruction of an object. The imaging system includes a power source that is configured to provide a variable high voltage. The imaging system includes a distributed X-ray source. The distributed X-ray source includes an array of X-ray emitters that allows fast switching "ON" and "OFF" using X-ray emitter grid electrode. The distributed X-ray sources is configured to generate an X-ray beam with an energy spectrum based on the variable high voltage and uses additional X-ray filters. The imaging system includes a controller. The controller is configured to operate synchronously with the change of the variable high voltage. The controller is configured to control a timing of when to engage an X-ray emitter of the array of X-ray emitters of the distributed X-ray source based on a predefined firing pattern.

20 Claims, 13 Drawing Sheets

(51) Int. Cl.
*A61B 6/40* (2024.01)
*A61B 6/42* (2024.01)

(52) U.S. Cl.
CPC .......... *A61B 6/4042* (2013.01); *A61B 6/4241* (2013.01); *A61B 6/4476* (2013.01); *A61B 6/54* (2013.01); *A61B 6/56* (2013.01)

(58) Field of Classification Search
CPC ........... A61B 6/4476; A61B 6/54; A61B 6/56; A61B 6/40; A61B 6/032; H05G 1/32; H05G 1/70
See application file for complete search history.

(56) References Cited

U.S. PATENT DOCUMENTS

| | | | | |
|---|---|---|---|---|
| 2005/0190882 | A1* | 9/2005 | McGuire | G01N 23/087 378/45 |
| 2011/0248727 | A1* | 10/2011 | Krumme | H02J 50/50 324/652 |
| 2015/0207415 | A1* | 7/2015 | Caiafa | H05G 1/58 363/21.02 |
| 2015/0282774 | A1* | 10/2015 | Lee | A61B 6/032 378/8 |
| 2016/0256128 | A1 | 9/2016 | Wang et al. | |
| 2017/0196522 | A1 | 7/2017 | Gupta et al. | |
| 2019/0325617 | A1 | 10/2019 | Kessener et al. | |
| 2020/0245962 | A1* | 8/2020 | Ganguly | G21K 1/10 |

FOREIGN PATENT DOCUMENTS

| | | | | |
|---|---|---|---|---|
| DE | 102009051897 | * | 5/2011 | ............ A61B 6/488 |
| DE | 102009051897 A1 | * | 5/2011 | ............ A61B 6/488 |
| KR | 102091512 | * | 3/2020 | ............. A61N 5/00 |
| KR | 102091512 B1 | * | 3/2020 | ............. A61N 5/00 |
| WO | WO2021064704 | * | 4/2021 | ............ A61B 6/547 |
| WO | WO 2021064704 A2 | * | 4/2021 | ............ A61B 6/547 |
| WO | WO 2021116003 | * | 6/2021 | ........... A61B 6/4042 |
| WO | WO 2021116003 A1 | * | 6/2021 | ........... A61B 6/4042 |

* cited by examiner

SPECTRAL X-RAY IMAGING USING VARIABLE HIGH VOLTAGE X-RAY SOURCE

CROSS-REFERENCE TO RELATED APPLICATIONS

This application claims the benefit of priority under 35 U.S.C. § 120 to U.S. Provisional Patent Application Ser. No. 63/235,947, entitled "SPECTRAL X-RAY IMAGING USING VARIABLE HIGH VOLTAGE X-RAY SOURCE," filed on Aug. 23, 2021, and U.S. Provisional Patent Application Ser. No. 63/279,371, entitled "SCANNING SPECTRAL X-RAY IMAGING USING VARIABLE HIGH VOLTAGE X-RAY SOURCE," filed on Nov. 15, 2021, the entire contents both applications are incorporated herein by reference.

BACKGROUND

1. Field

This specification relates to a system for executing a high-speed tomographic X-ray examination of objects using multiple X-ray beams with different spectra.

2. Description of the Related Art

X-ray imaging is typically performed by producing X-ray radiation, directing it onto the object of examination and capturing the X-ray radiation that passes through the object using various detection technologies. The generation of X-rays has traditionally been performed with a high voltage placed across an anode-cathode vacuum gap, which accelerates electrons from the cathode into the anode. The electrons decelerate in the anode material and produce Bremsstrahlung ("braking radiation") X-rays, which form a continuous spectrum that is distributed across a range of energies, an example of which is shown in FIG. 1. FIG. 1 shows the typical Bremsstrahlung X-ray spectrum when 70 kVp is applied to the X-ray source. The continuous Bremsstrahlung spectrum may also carry additional peaks of characteristic emission of the anode material. The high voltage that is applied to the anode-cathode gap may be altered to change the range of X-ray photon energies, an effect that is used to optimize the energy dependent attenuation of X-rays in the object under examination.

Some technologies use "spectral imaging." Spectral imaging measures the energy of the X-ray photons captured by the X-ray detector. With information about the photon energies, analysis of the materials through which the X-ray photons have passed may be obtained, which may be used to increase the diagnostic capability of various X-ray imaging modalities. For example, in Computed Tomography (CT), this additional information can be used for facilitating differentiation of tumors and other diseases from healthy tissue by using contrast agents with specific attenuation properties.

The challenges of combining spectral X-ray imaging with 3D imaging are significant and are currently resolved at premium cost only by spectral CT machines. However, the spectral CT modality is limited in its applicability to multiple X-ray medical applications—breast cancer screening, orthopedics, pediatric and neonatal X-ray imaging, cardiology, and so on. For example, spectral CT is not suited to the specific patient positioning requirements of breast cancer screening. Spectral CT is also not applicable to real-time X-ray imaging applications, like fluoroscopy, minimally invasive surgery, and others, which require access to the patient during the imaging session. At this time, there are no technologies available for performing spectral 3D X-ray imaging for a majority of traditional medical diagnostic modalities.

Systems that employ spectral X-ray detectors may carry a significant cost premium, which impedes widespread adoption of spectral X-ray imaging. The complexity and the additional cost come from the X-ray image acquisition subsystem, which needs to be capable of clinically acceptable spectrometric performance. These acquisition systems may employ photon counting X-ray detectors that exploit the direct detection principle of capturing the X-rays, which drives up the inherent costs. Charge sharing is an additional challenge of the direct detection photon counting systems. Charge sharing is the activation of multiple adjacent pixels by a signal produced by one detected X-ray photon, which reduces the resolution of the resulting image.

Some designs use kV switching to perform spectral imaging at different energies. For example, kV switching adjusts the applied high voltage to generate different energy exposures from the same X-ray source, as illustrated in FIG. 2. FIG. 2 shows typical X-ray spectra generated by kV switching between 50 kVp and 70 kVp. kV switching, however, limits the selection of high voltage levels based on the complexity of the high voltage switching hardware and the time required to switch voltage levels, which can introduce motion artifacts in the image. As a result, kV switching may be limited to the imaging of static objects.

Accordingly, there is a need for a system, apparatus, and/or method for spectral X-ray imaging technology suitable for performing high resolution, 3D captures and visualization of dynamic objects and processes.

SUMMARY

In general, one aspect of the subject matter described in this application is embodied in an imaging system. The imaging system includes a power source. The power source is configured to provide a variable high voltage. The imaging system includes a distributed X-ray source coupled to the power source. The distributed X-ray source includes an array of X-ray emitters. The distributed X-ray sources is configured to generate an X-ray beam with an energy spectrum based on the variable high voltage. The imaging system includes a controller coupled to the power source and the distributed X-ray source. The controller is configured to sense and control the variable high voltage. The controller is configured to control a timing of when to engage an X-ray emitter of the array of X-ray emitters of the distributed X-ray source based on a predefined firing pattern.

These and other embodiments may optionally include one or more of the following features. The controller may be configured to synchronize the timing of when to engage the X-ray emitter with the variable high voltage. The timing may be adjusted based on a feedback signal from the distributed X-ray source. The timing of when to engage each X-ray emitter of the array of X-ray emitters may be different from the other X-ray emitters and may be based on a change of the variable high voltage.

The power source may be an Alternating Current (AC) generator. The variable high voltage source may be a combination of direct current and alternating current. The imaging system may include a step-up transformer. The step-up transformer may be coupled to the power source and the distributed X-ray source. The step-up transformer may be configured to receive the variable high voltage and output a second voltage that is greater than the variable high voltage. The variable high voltage may use an alternating current (AC) power line frequency.

The imaging system may include multiple X-ray filters. The multiple X-ray filters may be configured to receive the X-ray beam with the energy spectrum as produced by the array of X-ray emitters. The multiple X-ray filters may reduce or eliminate lower energy X-ray photons within the energy spectrum so that an amount of energy delivered is reduced without affecting image quality. The multiple X-ray filters may be configured to use K-edge absorption phenomenon for spectral adjustments.

In another aspect, the subject matter is embodied in a method of performing real-time spectral tomographic reconstruction of an object. The method includes providing, by a power source, an adjustable or alternating voltage to a plurality of X-ray emitters of an X-ray source. The method includes selecting, by a controller, an X-ray emitter from among a plurality of X-ray emitters to generate an X-ray beam with an energy spectrum from the adjustable or alternating voltage when the adjustable or alternating voltage is within a specific range. The method includes generating, by the X-ray source, a plurality of X-ray beams with multiple energy spectra.

These and other embodiments may optionally include one or more of the following features. The method may include filtering, using one or more filters, the X-ray beam energy spectrum to remove lower energy photons or to emphasize specific energy spectrum characteristics. The method may include detecting, using an X-ray detector, the multiple X-ray beams created by the X-ray source in rapid succession to form images. The multiple X-ray filters may use K-edge absorption phenomenon for spectrum adjustments. The method may include reconstructing the image into a tomographic image, including real-time reconstruction configuration. The method may include providing the tomographic image data to a user.

BRIEF DESCRIPTION OF THE DRAWINGS

Other systems, methods, features, and advantages of the present invention will be apparent to one skilled in the art upon examination of the following figures and detailed description. Component parts shown in the drawings are not necessarily to scale and may be exaggerated to better illustrate the important features of the present invention.

DETAILED DESCRIPTION

Disclosed herein are systems, X-ray sources, filters, detectors, and methods for creating real-time 3D tomographic images. Particular embodiments of the subject matter described in this specification may be implemented to realize one or more of the following advantages. The imaging system has an X-ray source that may drive rapid pulses at a selected time period corresponding to a specific voltage on variable high voltage waveform. In this manner, multiple shots may be generated at the same high voltage, or a series of different spectra may be generated by selecting different time periods corresponding to different high voltages. Moreover, the amplitude and the frequency of the alternating voltage may be selected to control the rate and spectral separation of the pulsed X-ray source. This allows the generation of images using different energy spectra without the complexity of multiple power supplies or fast kV switching and may allow the imaging system to operate in spectral imaging mode.

Moreover, an array of X-ray emitters may be used and controlled by an array of synchronized spectral selection triggers. Using the array of synchronized spectral selection triggers and/or the array of X-ray emitters, either cold cathode or thermionic, makes it possible to select which emitter will be turned on at which time to control the X-ray spectrum produced by a given X-ray emitter. This allows the generation of spectral angular tomographic information of the object of examination in a very short period of time. Active pixel CMOS X-ray detectors are capable of capturing the X-ray images at required speeds. The spectral angular tomographic information of the object may be computationally processed to create a 3D model of the object which may be further subjected to various analytical processing methods that are dependent on the imaging application.

Figure 1:
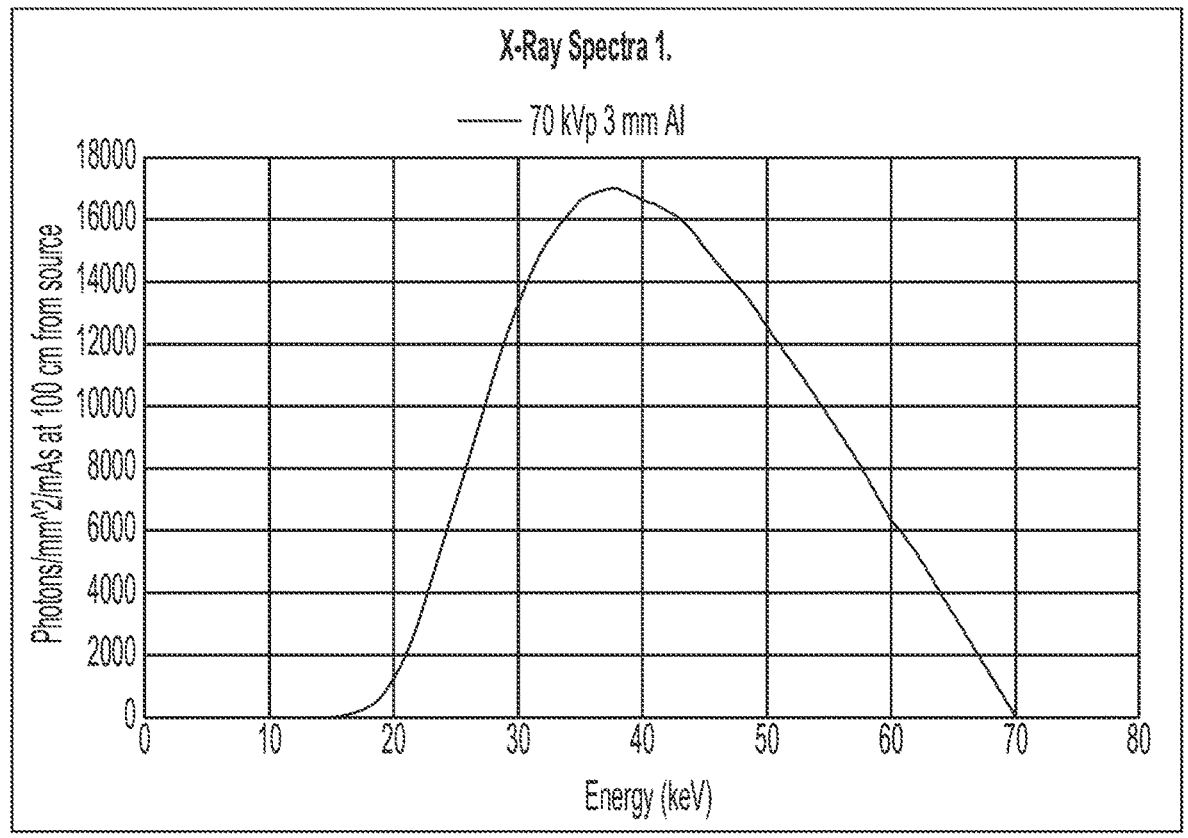
FIG. 1 shows an example graph of a typical Bremsstrahlung X-ray spectrum when 70 kVp is applied to the X-ray source.
Figure 2:
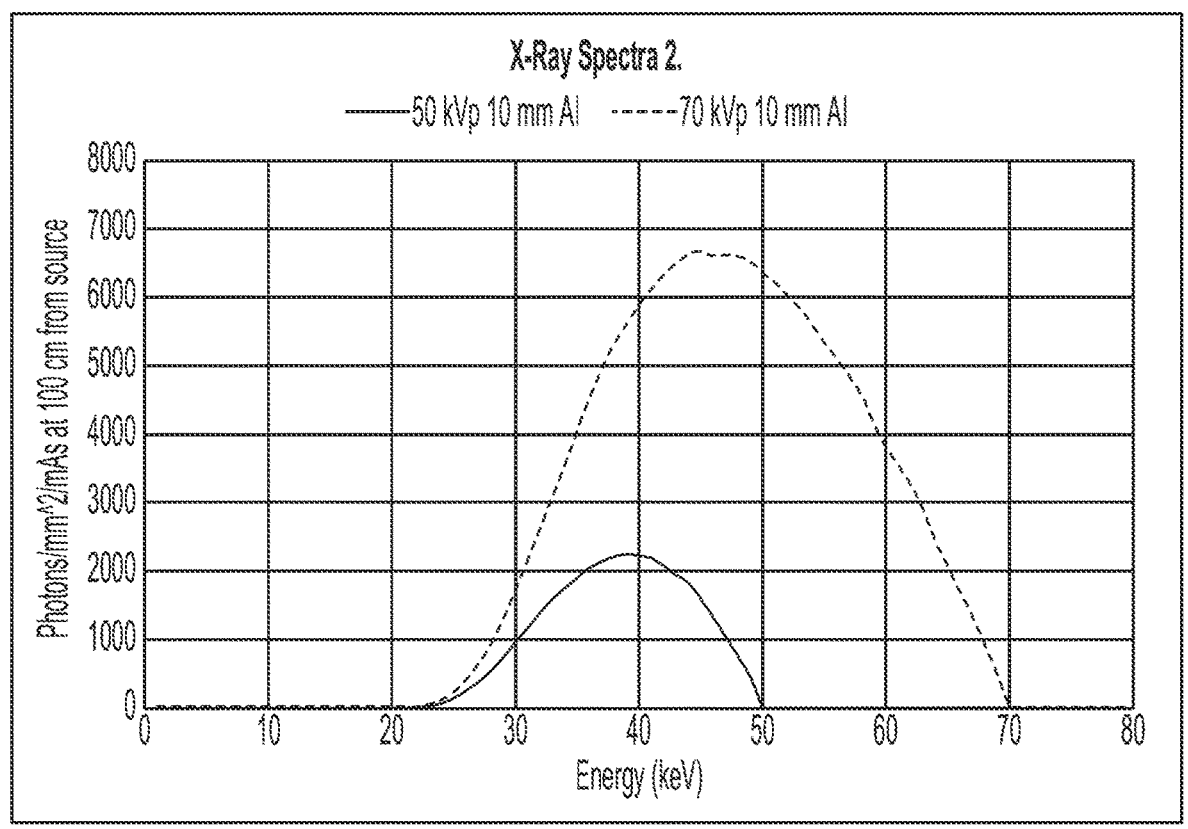
FIG. 2 shows an example graph of a typical X-ray spectra generated using kV switching between 50 kVp and 70 kVp.
Figure 3:
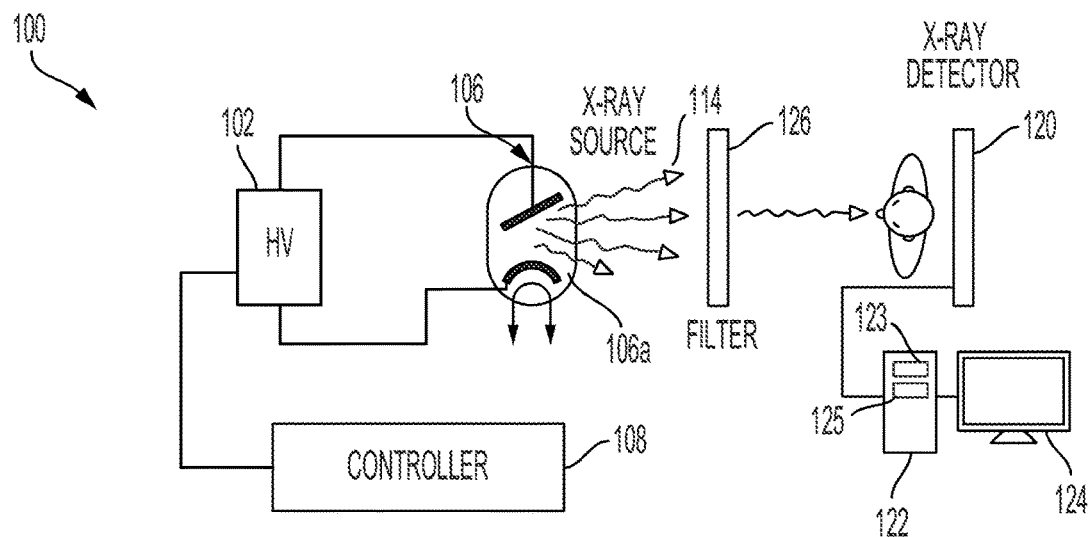
FIG. 3 shows a spectral imaging system using a single X-ray source according to an aspect of the invention.
Figure 3:
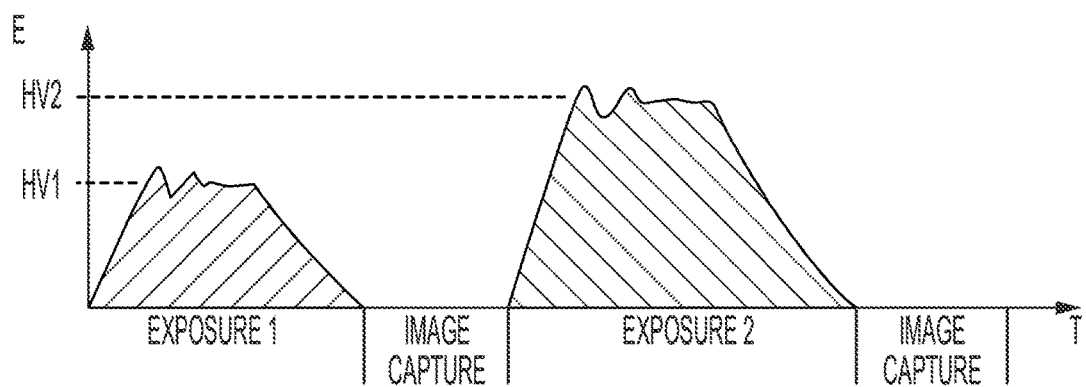

FIG. 3 shows a typical 'kV switching' spectral imaging system 100. The imaging system 100 includes a high voltage (HV) power source 102, two-electrode X-ray source 106 with an X-ray emitter 106a, a controller 108, an additional filter 126, an X-ray detector 120 and/or a computing device 122. An imaging system 100 that uses kV switching may not generate significantly different X-ray spectra with a change of HV only. The imaging system 100 emits X-rays during the time when the HV is applied to the X-ray source 106, which may affect the quality of the X-ray beam during the rising and falling edges of the HV pulse.

Figure 4:
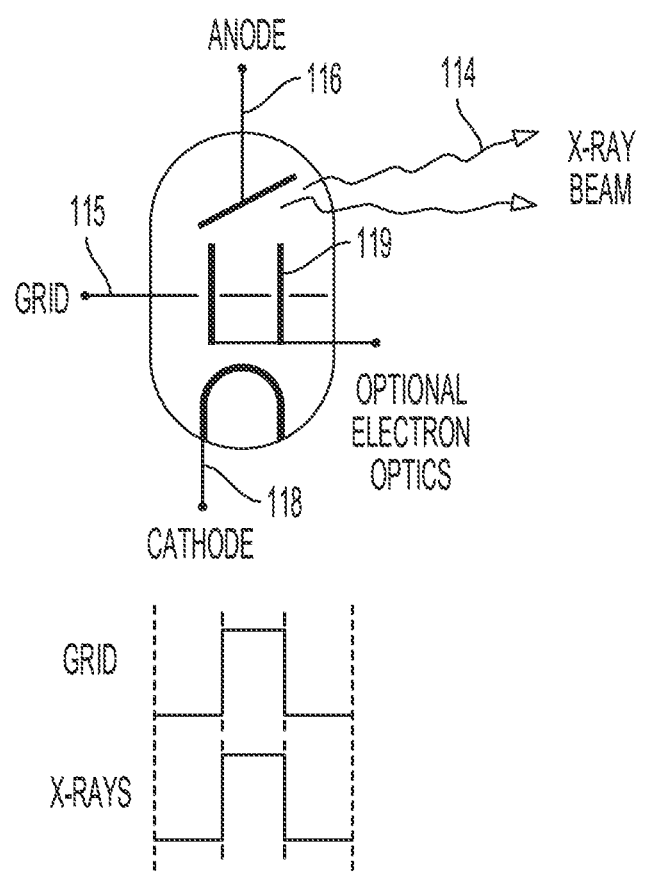
FIG. 4 shows an X-ray source with a third electrode for controlling electron flow between the anode and the cathode to shape the X-ray beam according to an aspect of the invention.

As shown in FIG. 4, the imaging system 100 may control the production of X-ray radiation through the addition of a third electrode placed between the cathode 118 and the anode 116, which works as a switching mechanism for the electron current between the cathode and the anode. This third electrode may be called a "grid" 115. When a first voltage is placed on the grid 115, the flow of electrons from the cathode 118 to the anode 116 may be stopped, preventing the production of X-ray radiation. When a second voltage is applied to the grid 115, the electrons accelerate through the grid 115 and the X-ray source 106 produces X-ray beam 114. The imaging system 100 may operate to produce the X-ray beam based on the timing of the HV voltage and grid control. Therefore, the imaging system 100 is capable of rapid "ON" and "OFF" switching of the X-ray beam.

The imaging system 100 may produce short X-ray pulses and may comprise X-ray sources, which employ non-thermionic or "cold" cathodes. These types of devices by design employ the three-electrode X-ray emitter structure. Advanced non-thermionic electron emitting technology, e.g., Carbon Nano Tubes, also enables practical multi-emitter X-ray sources for 3D X-ray imaging due to reduced mechanical and thermal constraints compared to standard thermionic technology. Sources of this type have the capability to switch rapidly, facilitating the concept of selecting a time period where the variable high voltage would be of a specific value and triggering the source "ON" and "OFF" during these time periods would create multiple spectra in rapid succession. This allows for an imaging system that may produce rapidly changing X-ray spectra. If coupled with a detector of sufficiently high frame rate, the result may be a fast spectral imaging system with a single image chain and a single variable high voltage power supply.

The electrons flowing from the cathode 118 to the anode 116 may impact the anode 116 in a defined area with a specific geometry. This impact area geometry may generate an X-ray beam 114 for a particular application. The imaging system 100 may employ a passive, fixed, or variable device or component 119 to focus the electron beam onto the impact area of the anode 116, creating an X-ray beam 114, for the particular application.

The imaging system 100 may have one or more additional filters 126. The X-ray source 106 may emit the X-ray beam 114 through additional filter(s) 126 that have a controlled thickness and/or composition, which may change the spectrum of the X-ray beam. This may provide additional control over the X-ray spectrum produced by the X-ray source 106.

The additional filter(s) 126 may be made out of aluminum as this metal exhibits monotonous dependence of attenuation vs. X-ray photon energy in the diagnostic range of X-ray beam energies. Additional X-ray filters of this type are called 'absorption' X-ray filters. As X-ray imaging applications vary with respect to the optimal X-ray spectrum to achieve the best X-ray contrast, it is desirable to use different X-ray beam filtration for different X-ray imaging applications. When the thickness of absorption X-ray additional filter 126 is increased, the low energy X-ray photons are attenuated more than the high energy X-ray photons which results in average energy of the X-ray spectrum shifting towards higher values. This spectral "hardening" reduces the soft energies in the X-ray spectrum which are highly likely to be absorbed by the object and may not reach the X-ray detector 120. In medical imaging, reducing, or eliminating the lower energy X-ray photons reduces the overall dose to a patient without affecting the image quality.

Some materials with high atomic numbers may be used in X-ray filtering to modify the high energy content of the X-ray spectrum. For example, the materials may be a metal, such as tungsten, tin, silver, and others, which have an increased absorption above specific X-ray energies. If additional X-ray filter(s) 126 made out of this material are inserted into the X-ray beam, a sharp cut-off of the high energy part of the spectrum may be achieved. The rearrangement of the structure of electron shells in the metal atom when the excitation energy of the X-ray photons exceeds the binding energies of the electrons in different electron shells of the atom results in a sharp X-ray absorption increase at energy of X-ray photons which is unique for a specific element. The transition from L-shell to K-shell may have a characteristic energy which falls into the X-ray energy range of interest, which may be referred to as 'K-edge absorption.' K-edge absorption additional filters also provide filtering for the soft X-rays in the spectrum of the X-ray beam and may provide more control of the X-ray spectrum as compared to absorption filters only.

The imaging system 100 may include an X-ray detector 120 and/or a computing device 122. The X-ray detector 120 may be used to capture X-ray images. The X-ray detector 120 may provide the captured X-ray images to the computing device 122 to analyze and/or process. The computing device 122 may include one or more processors, such as the processor 123 of the computing device 122. The one or more processors may execute instructions stored in one or more memory, such as the memory 125 of the computing device 122, to control the power source 102 or to construct the X-ray image.

The computing device 122 may include a user interface 124. The user interface 124 may include an input/output device that receives user input, such as a user interface element, a button, a dial, a microphone, a keyboard, or a touch screen, and/or provides output, such as a display, a speaker, an audio and/or visual indicator. The user interface 124 may receive user input that may include configuration settings. The display of the user interface 124 may present or provide information to the operator, such as the composition of the material of the object.

Figure 5A:
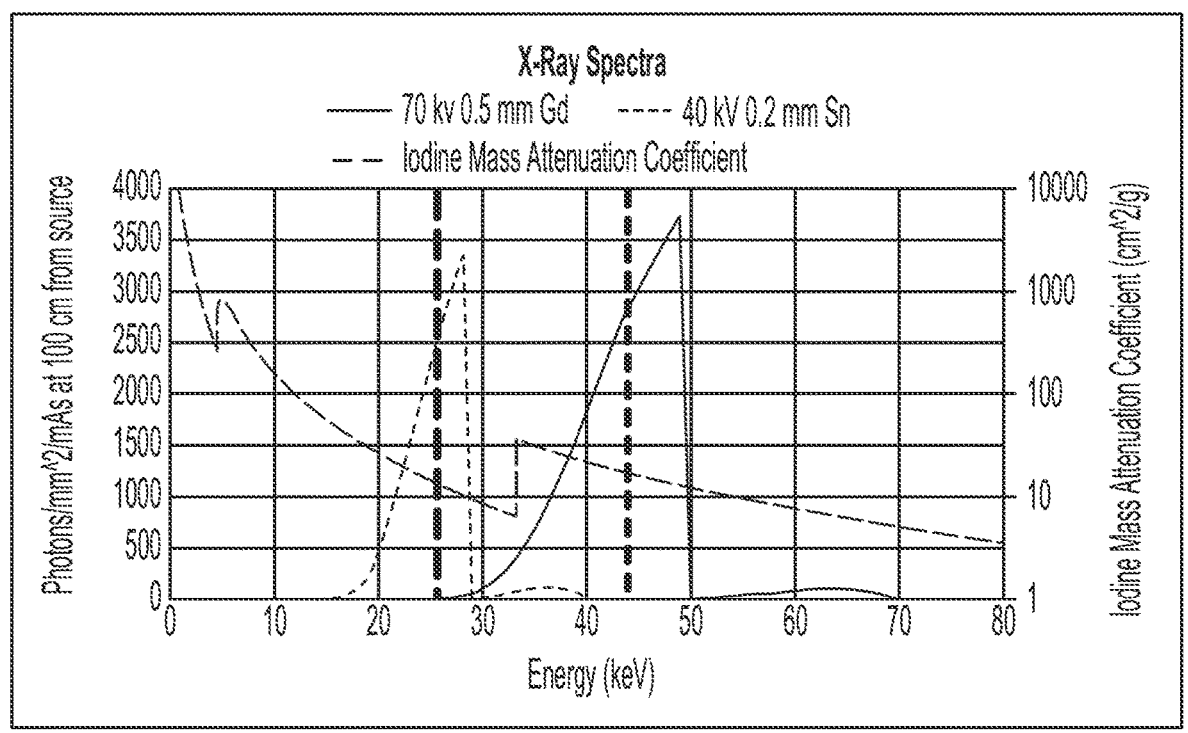
FIG. 5A shows an example graph of spectra designed to identify iodine content in an object using a spectral imaging system according to an aspect of the invention.
Figure 5B:
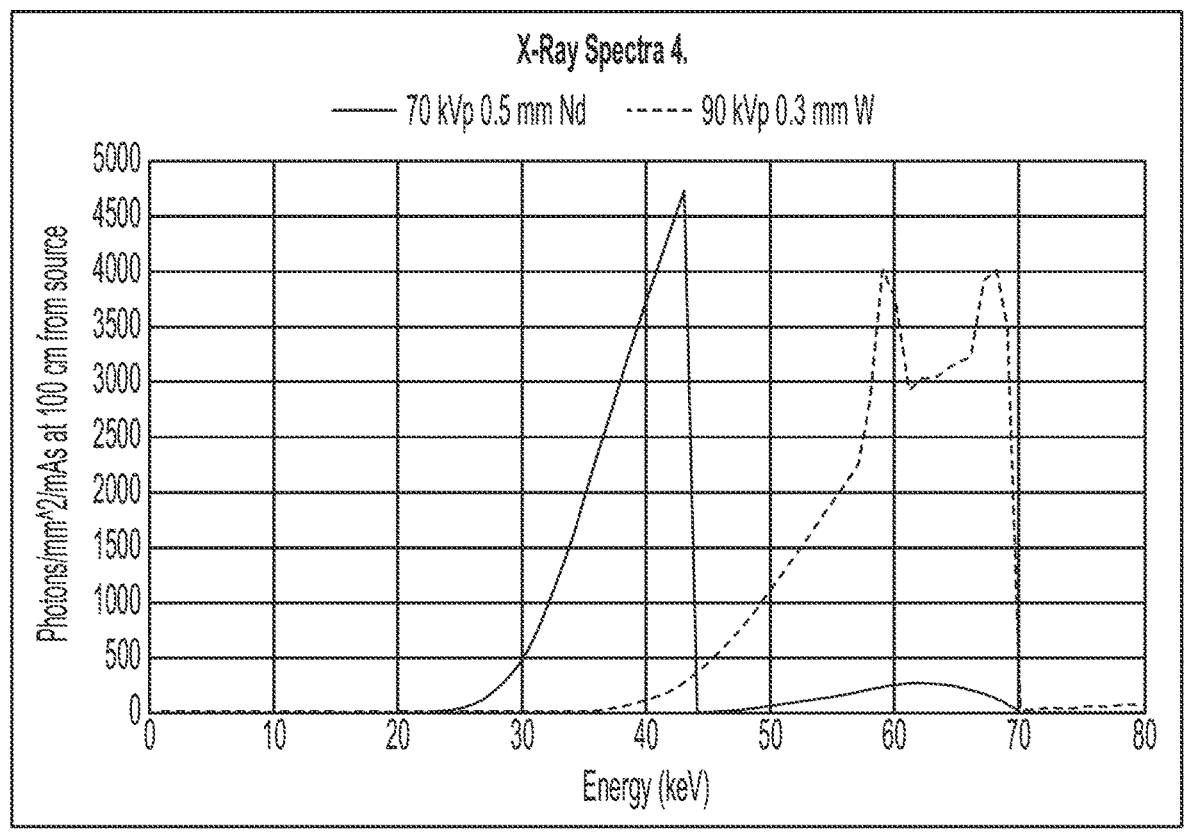
FIG. 5B shows an example graph of spectra designed to identify gadolinium content in the object using a spectral imaging system according to an aspect of the invention.

FIGS. 5A-5D show graphical representations of the X-ray spectra that may be produced by the imaging system 100 using a K-edge absorption filter(s). In FIG. 5A, the additional filter used for the 70 kVp exposure is 0.5 mm gadolinium, while the additional filter for the 40 kVp exposure is 0.2 mm tin. These voltage and additional filter combinations will produce X-ray energy spectra with an average energy of approximately 43.9 keV and 25.6 keV, respectively. FIG. 5A also shows an iodine absorption curve. Using these two spectra, two images may be created with iodine emphasized in one and not in the other. The difference between these images is then the iodine alone. FIG. 5B shows values of applied to the X-ray source high voltage and K-edge absorption filter design which may be used to identify gadolinium using the same principle. Iodine and gadolinium are common contrast agents used in medical imaging. The ability to identify the location of these contrast agents in the body provides clinical data for the radiologist. While these HV and additional filter combinations may be capable of discriminating these materials in clinical practice, using them with a single X-ray source 106 requires means to switch the filters between exposures. The additional filter switching time delay between the exposures, however, may generate motion artifacts and lengthens the examination.

Figure 5C:
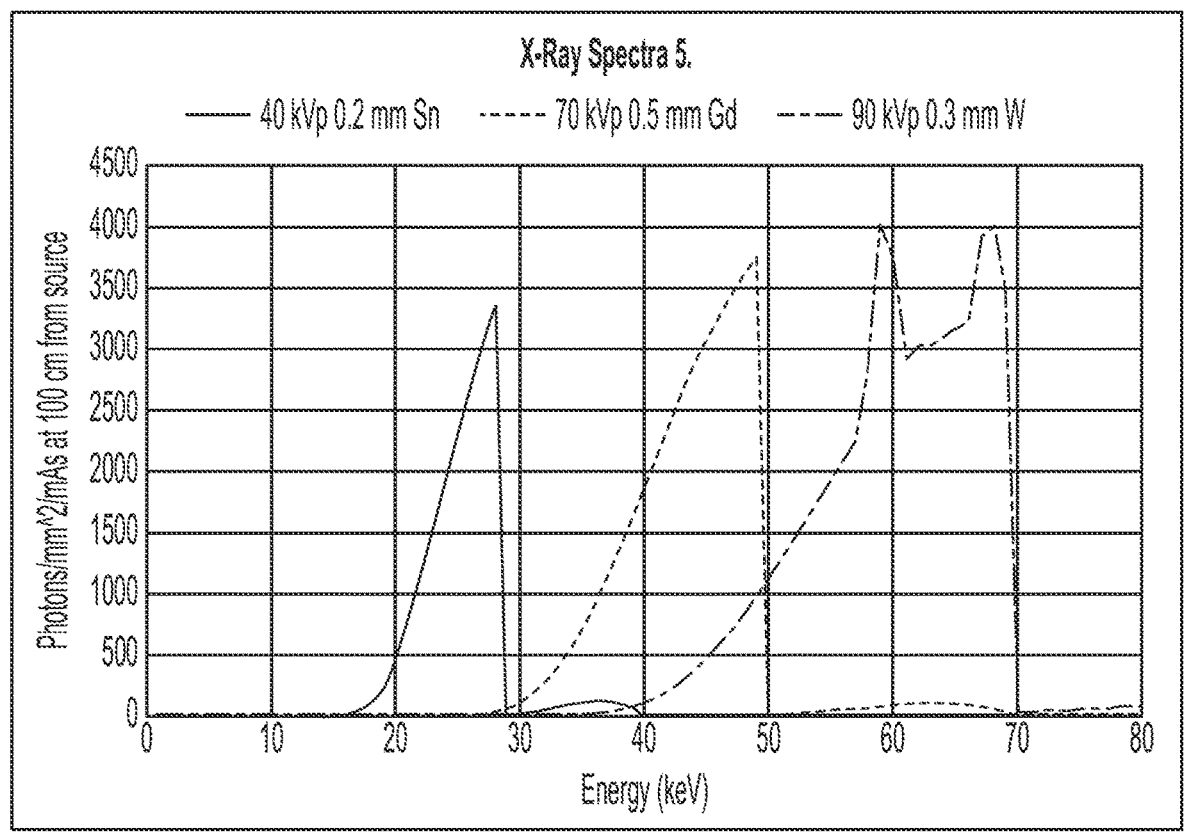
FIG. 5C shows an example graph of spectra designed to enable three energy imaging for material decomposition and identification using a spectral imaging system according to an aspect of the invention.

The imaging system 100 may vary the high voltage applied to the X-ray source 106 and select one or more K-edge absorption filters to produce X-ray beams that exhibit minimal spectral overlap and may be used effectively for spectral imaging. FIG. 5C shows a non-overlapping X-ray spectra produced using the X-ray source 106 if the X-ray beams produced at 40 kVp, 70 kVp, and 90 kVp are filtered with a 0.2 mm tin filter, a 0.5 mm gadolinium filter, and a 0.3 mm tungsten filter, respectively. This provides for improved material identification based on analysis of the object's attenuation of the three non-overlapping X-ray spectra.

Figure 5D:
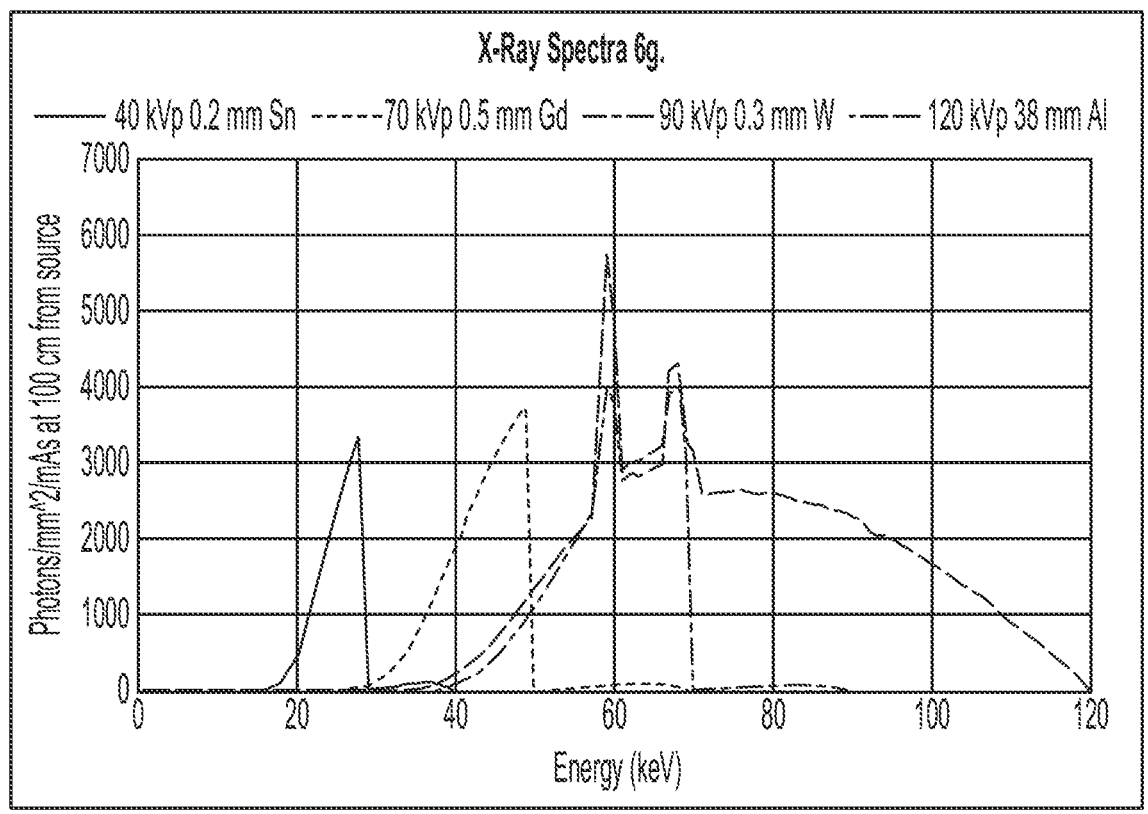
FIG. 5D shows an example graph of spectra designed to enable four energy imaging for material decomposition and identification using a spectral imaging system according to an aspect of the invention.

FIG. 5D shows one of the possible techniques to increase the number of energy spectra above three. In FIG. 5D, the imaging system 100 may use four different HV and additional filtration combinations: 40 kVp, 70 kVp, 90 kVp, and 120 kVp and the additional filters respectively are 0.2 mm tin, 0.5 mm gadolinium, 0.3 mm tungsten, and 38 mm aluminum. The difference between the imaging results produced with 120 kVp and a 35 mm aluminum additional filter and 90 kVp with a 0.3 mm tungsten additional filter may be representative of the exposure produced by a separate X-ray beam with the fourth non-overlapping spectrum starting at approximately 70 keV. Other HV and additional filtration combinations using K-edge absorption additional filters and absorption additional filters may be also designed to address specific needs of various X-ray imaging applications.

Figure 6:
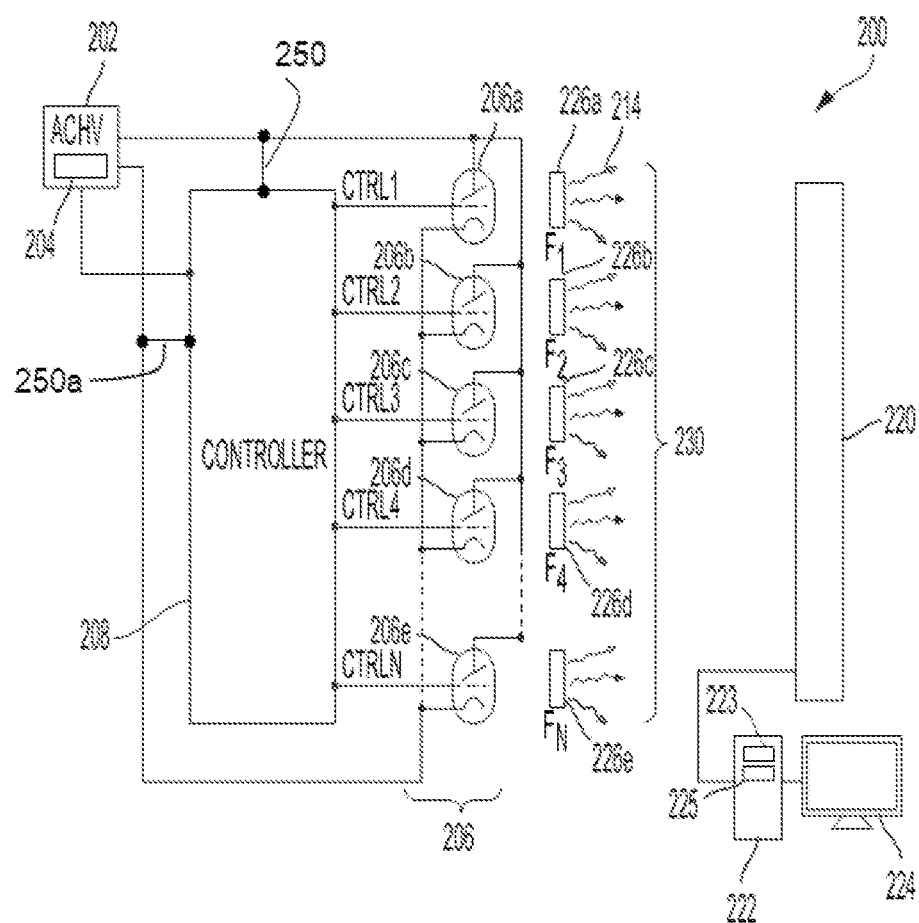
FIG. 6 shows an example schematic of a spectral imaging system that employs a distributed X-ray source according to an aspect of the invention.

An imaging system 200 that has a distributed X-ray source 206, as shown in FIG. 6 for example, may provide fast switching between different X-ray spectra in generated X-ray beams. For this instance, imaging system 200 employs a distributed X-ray source 206 and distributed array of additional X-ray filters 230.

Figure 7:
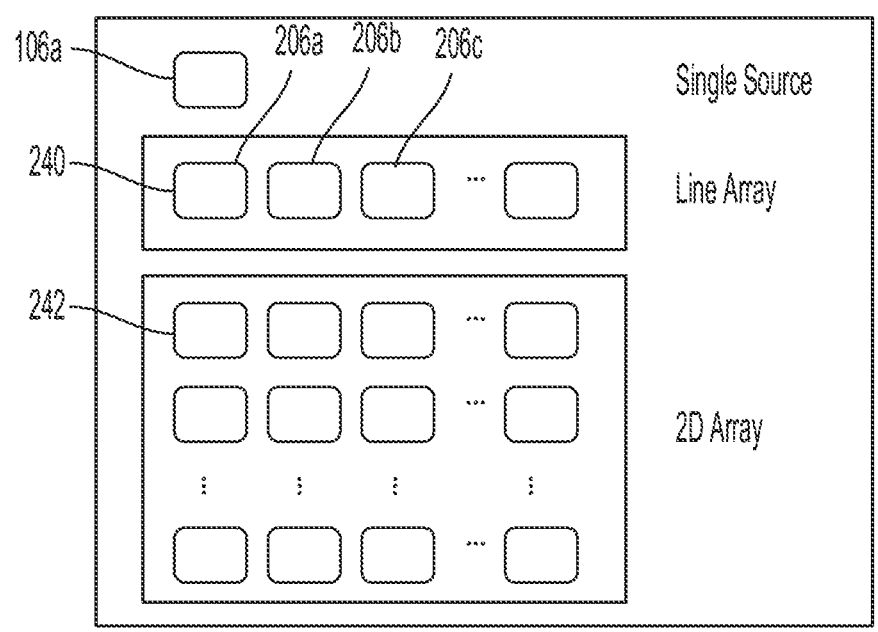
FIG. 7 shows an example of different configurations of a distributed X-ray source array of a spectral imaging system according to an aspect of the invention.

The distributed X-ray source 206 may be arranged or positioned in a two-dimensional (2D) array 242 or in a line array 240, as shown in FIG. 7 for example. Each of the X-ray emitters 206a-e may be positioned at a different location or position surrounding the object and/or may be positioned or moved using an actuator to be directed at the same or different location or position surrounding the object. The X-ray source 206 may be coupled to a single controller or to multiple different controllers that select or trigger the activation of the electron flow through the corresponding cathode of the selected or triggered X-ray source. This allows generating spectral angular tomographic information of the object of examination in a very short period of time.

The imaging system 200 may be used for dual energy 3D X-ray imaging or for multi-energy 3D X-ray imaging. The imaging system 200 may include a variable high voltage power source 202, a distributed X-ray source 206 having N grid-controlled X-ray emitters 206a-e, a feedback signal 250 and 250a to monitor the variable high voltage at the distributed x-ray source, and/or a filtering device 230 that has a set of additional filters 226a-e, which are aligned with individual X-ray emitters 206a-e of the X-ray source 206 and use absorption filtering and/or K-edge filtering. The imaging system 200 may include a controller 208, a detector 220 and/or a computing device 222. Typically, X-ray emitters with grid control of X-ray emission may be operated with sub-millisecond timing resolution, which is at least an order of magnitude faster than the high voltage switching times of the current X-ray high voltage power supplies. Because of that, the speed of switching between the different X-ray spectra for imaging system 200 is determined by the speed of high voltage adjustments of the high voltage power source 202.

The imaging system 200 includes the power source 202. The power source 202 may be an Alternating Current (AC) generator. The controller 208 may be coupled to the power source 202 and may monitor, control, and/or adjust the adjustable voltage so that different energy spectrums may be produced. The AC generator may provide the voltage in the form of various waveforms, frequencies, and/or amplitudes based on application needs for the imaging system 200.

The AC generator may include or be coupled to a step-up high voltage transformer 204 operated at standard AC power line frequencies, in this case the output high voltage of the power source 202 may be a sine wave with the standard frequency of the AC power line. The diagnostic X-rays in medical imaging may use a high voltage in the range of 40 kV-150 kV. This voltage range may be used for other applications, e.g., in security, food processing, or non-destructive testing. The imaging system 200 may facilitate rapid high voltage change at the distributed X-ray source 206, which may enable real-time 3D spectral X-ray imaging.

Figure 8:
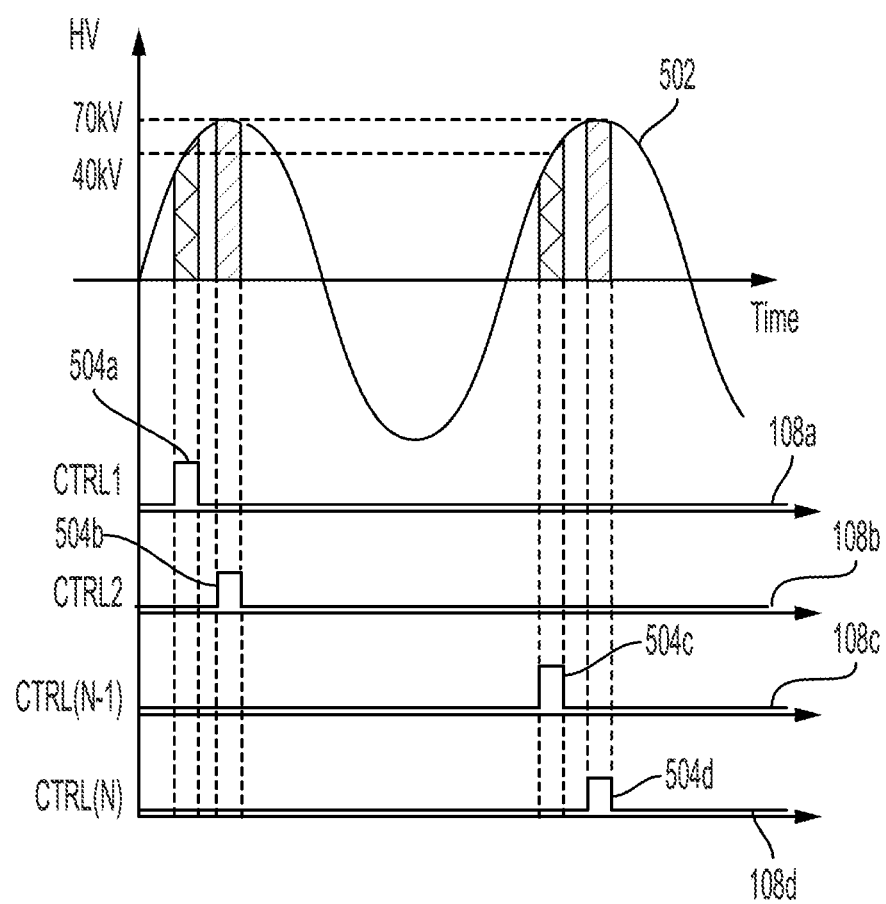
FIG. 8 shows an example control process to generate multiple different X-ray spectra using the spectral imaging system of FIG. 6 according to an aspect of the invention.

The step-up transformer 204 may provide an alternating high voltage that may be approximately 70 kVp sine wave 502 running at standard AC line frequency, as shown in FIG. 8 for example. The controller 208 may be synchronized with the AC line frequency and may select and/or trigger an X-ray emitter at different time intervals 504a-d. For example, a first X-ray emitter is turned "ON" when the cathode of the first X-ray emitter is enabled during the time interval 504a by the control pulse CTRL1, which corresponds to approximately 40 kVp applied to the X-ray source. The controller 208 may adjust the timing based on a feedback signal 250 and 250a to ensure that the time interval delivers the desired variable HV to the X-ray emitter. The same variable HV may be applied to all X-ray emitters in the distributed X-ray source 206 but only the emitter enabled by controller 208 may produce an X-ray beam. The additional filter 226a-e associated with this emitter may be designed to achieve specific filtration of the X-ray beam. Therefore, during time interval 504a, a first X-ray beam with a first energy spectrum may be produced. Subsequently, controller 208 may trigger a second X-ray emitter during time interval 504b, which corresponds to approximately 70 kVp applied at the X-ray source. The additional filter 226a-e associated with the second X-ray emitter may be designed to produce a different X-ray spectrum filtration compared to the first X-ray beam, therefore, a second generated X-ray beam may have a different X-ray spectrum.

In some implementations, the high voltage may not be constant during time intervals 504a and 504b. As mentioned, the K-edge filtering technique may alter the spectrum according to the individual properties of the additional filter material and therefore the K-edge additional filter may also reduce the impact on the X-ray beam spectrum from the varying HV during the time interval that the X-ray emitter is 'ON.'

Further, the controller 208 may operate pairs or two or more of the X-ray emitters 206a-e in the distributed X-ray source 206 according to the time intervals 504a and 504b until the last pair of X-ray emitters are enabled by control pulses CTRL(N−1) 504c and CTRL(N) 504d. As a result, the imaging system 200 may produce two sets of X-ray exposures with alternating X-ray spectra between the exposures, each pair taken at different incident angles with respect to the object of examination. Therefore, the full timing of generating multiple spectral projections, such as for 10 spectral projections, for 3D reconstruction may be equivalent to approximately 10 periods of AC line frequency or 200 ms in the case of 50 Hz AC line and 167 ms for 60 Hz AC line. Thus, the imaging system 200 with a step-up transformer 204 may perform real-time imaging with a 3D information of the object captured with a frame rate up to 6 Hz.

The imaging system 200 may include a fast X-ray detector (or "detector") 220. The detector 220 may capture X-ray images at a high frame rate. The detector 220 may be an active pixel CMOS X-ray detector capable of capturing the X-ray images at the desired speeds. With the detector 220, the imaging system 200 may generate real-time spectral tomographic imaging of the object.

The detector 220 may capture images that are produced in a standard mode of operation for the detector 220. The resolution of the captured X-ray images may be dependent on the geometry of the imaging system 200 and the design of the detector 220. Therefore, the imaging system 200 may be deployed in imaging applications that require a higher or increased X-ray resolution, e.g., Digital Breast Tomosynthesis.

The imaging system 200 may include a computing device 222 and/or a controller 208. The computing device 222 may include the controller 208 and/or be separate from the controller 208. The computing device 222 and/or the controller 208 may include one or more processors, such as the processor 223 of the computing device 222. The one or more processors may execute instructions stored in one or more memory, such as the memory 225 of the computing device 222, to control the amount of the high voltage that is applied, select the one or more X-ray emitters 206a-e to capture the exposure of the one or more images, control a timing of the capture of the exposure and reconstruct the composition of the object to display or provide to an operator.

The computing device 222 may include a user interface 224. The user interface 224 may include an input/output device that receives user input, such as a user interface element, a button, a dial, a microphone, a keyboard, or a touch screen, and/or provides output, such as a display, a speaker, an audio and/or visual indicator. The user interface 224 may receive user input that may include configuration settings. The display of the user interface 224 may present or provide information to the operator, such as the composition of the material of the object.

Figure 9:
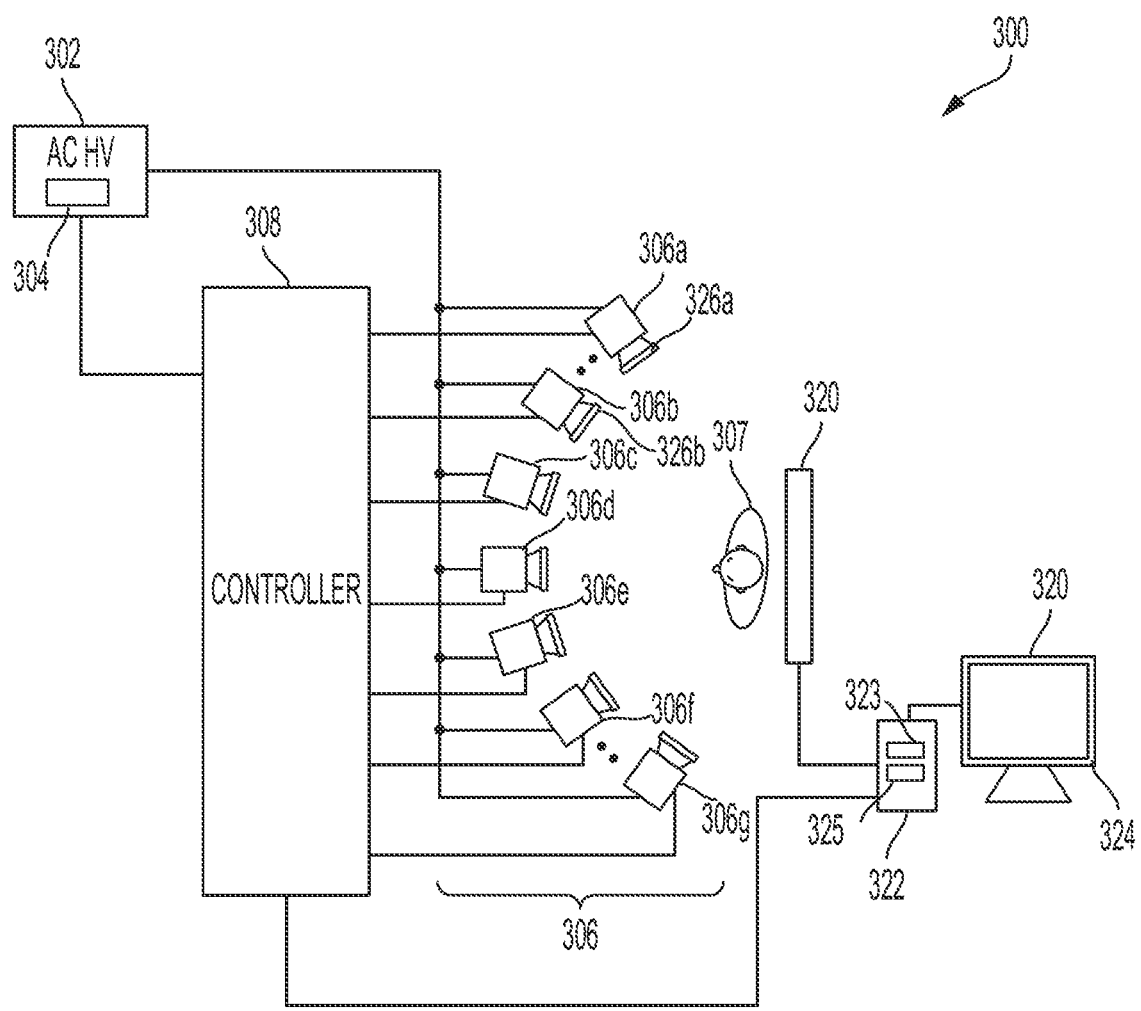
FIG. 9 shows an example spectral imaging system that is designed for dual-energy 3D spectral examinations according to an aspect of the invention.

FIG. 9 shows an imaging system 300. The imaging system 300 may have a variable high voltage source 302 that may be adjustable or alternating and have or be coupled to a step-up transformer 304, a controller 308 that is synchronized with the variation of high voltage source 302, and a distributed X-ray source 306 with multiple X-ray emitters 306a-g, fast X-ray detector 320 connected to a computing device 322. The computing device 322 may include a processor 323 and/or a memory 325. The processor and/or the memory 325 may have similar structure and/or functionality as the processor 123, 223 and/or the memory 125, 225.

The multiple X-ray emitters 306a-g of the X-ray source 306 may be positioned around or located at different locations or positions surrounding the object 307, which is being examined. The distributed X-ray source 306 may have or use multiple X-ray filters 326a-b. The multiple X-ray filters 326a-b may include multiple types or kinds, such as a first type of X-ray filter 326a and/or a second type of X-ray filter 326b, which are aligned to corresponding X-ray emitters 306a-g to filter the X-ray spectra generated by the X-ray emitters 306a-g. The first type of X-ray filter 326a may be designed to output a low energy X-ray beam by a combination of absorption and K-edge absorption materials, whereas the second type of X-ray filter 326b may be designed to output a high energy X-ray beam by a combination of absorption and K-edge absorption materials. The multiple X-ray filters 326a-b may be uniformly distributed across the corresponding X-ray emitters 306a-g.

The controller 308 may select time intervals from the alternating high voltage where the high voltage amplitude in combination with the multiple X-ray filters 326a-b may produce X-ray beams with the required spectral characteristics. The controller 308 may turn the X-ray emitters "ON" and "OFF" during these time intervals. The timing of the selection of the time intervals may be similar to the timing diagram shown in FIG. 8. The controller 308 may select one or more of the X-ray emitters 306a-g based on configuration data to image the object with enough spectral and angular variation to perform spectral tomographic imaging.

Figure 10:
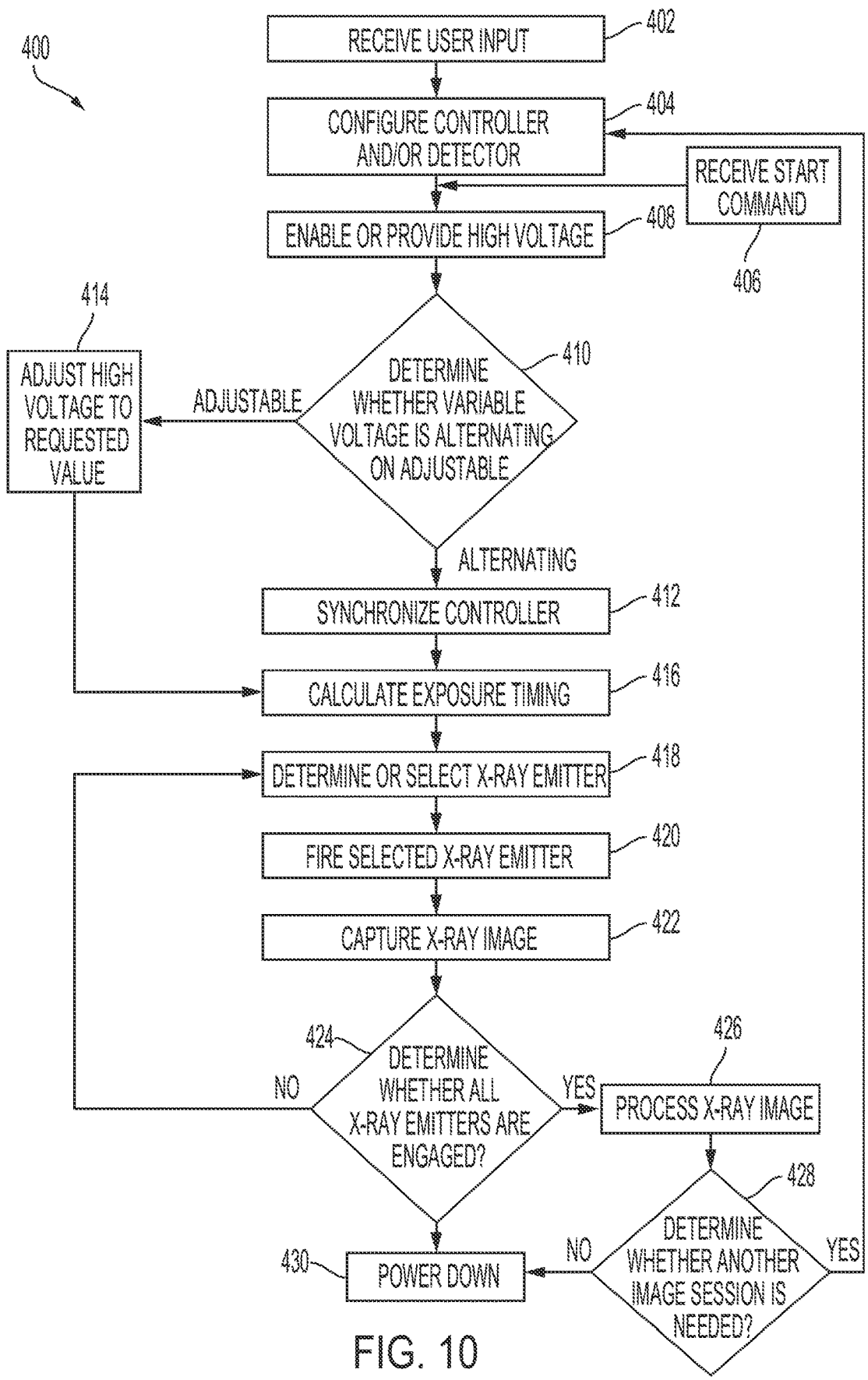
FIG. 10 is an example flow diagram of a process to perform a spectral 3D examination using the imaging system according to an aspect of the invention.

FIG. 10 is a flow diagram of the process 400 to perform a spectral 3D examination using the imaging system 200, 300. One or more computers or one or more data processing apparatuses, for example, the controller 208, 308 and/or the processor 223, 323 of the computing devices 222, 322 of the imaging systems 200, 300, appropriately programmed, may implement the process 400.

The imaging system 200, 300 receives user input (402). The user input may include one or more configuration settings for the one or more controllers 208, 308 and/or the one or more computing devices 222, 322. The user input may be received from an operator or a user and/or may be pre-loaded, pre-configured or otherwise pre-determined. Different configuration settings may be used for different imaging sequences. The user input may also include a power on signal that powers on the imaging system 200, 300. The user input may indicate the threshold number X-ray emitters 206a-e, 306a-g to be selected, used and/or fired. The imaging system 200, 300 may turn on when the power on signal is received and configure the controller 208, 308 and/or the detector 220, 320 based on the one or more configuration settings.

The imaging system 200, 300 configures the controller 208, 308 and/or the detector 220, 320 (404). The imaging system 200, 300 may configure the controller 208, 308 and/or the detector 220, 320 based on the one or more configuration settings. The one or more configuration settings may have been stored in the memory 225, 325. The imaging system 200, 300 may configure the power of the X-ray and the spectrum. The imaging system 200, 300 may configure the number of X-ray emitters 206a-e, 306a-g used.

The imaging system 200, 300 receives a start command (406). The imaging system 200, 300 may receive the start command from the user interface 224, 324. The start command may initialize the power source 202, 302 to power on the power source 202, 302 to provide the high voltage.

The imaging system 200, 300 enables or provides the high voltage (408). The power source 202, 302 turns on and provides a variable high-voltage, such as an alternating or adjustable high-voltage. The imaging system 200, 300 determines whether the variable high voltage is an alternating or adjustable voltage (410). When the variable high voltage is an alternating high voltage, the controller 208, 308 synchronizes the controller 208, 308 to the variable high voltage (412). The controller 208, 308 may be a slave and obtain the high voltage value from the power source 202, 302 and follow the high voltage value to synchronize with the variable high voltage. Whereas, when the variable high voltage is an adjustable high voltage, the controller 208, 308 sets the high voltage to a required value (414). The controller 208, 308 may be a master and may set or adjust the power source 202, 302 to provide the high voltage at the required value.

Once the controller 208, 308 is synchronized and/or the high voltage is adjusted to the required value, the imaging system 200, 300 calculates an exposure timing. The controller 208, 308 calculates the exposure timing to control the X-ray emitter 206a-e, 306a-g from among the one or more X-ray emitters 206a-e, 306a-g to produce the exposure (416). The imaging system 200, 300 may determine or select the X-ray emitter 206a-e, 306a-g based on the exposure timing to energize or fire the electrode of the X-ray emitter 206a-e, 306a-g (418).

The imaging system 200, 300 may fire the selected or determined X-ray emitter 206a-e, 306a-g (420). The variable high voltage is provided through the selected or determined X-ray emitter 206a-e, 306a-g so that the detector 220, 320 may capture an exposure of the image from the selected or determined X-ray emitter 206a-e, 306a-g.

The imaging system 200, 300 may capture the X-ray image (422). The detector 220, 320 may capture the X-ray image from the selected determined X-ray emitter 206a-e, 306a-g. The detector 220, 320 may capture or detect the X-ray beam from each of the one or more X-ray emitters 206a-e, 306a-g of the X-ray source 206, 306.

The imaging system 200, 300 determines whether all the X-ray emitters 206a-e, 306a-g have been engaged (424). The imaging system 200, 300 may determine whether the number of X-ray emitters 206a-e, 306a-g that have been fired is equivalent to the number of X-ray emitters 206a-e, 306a-g that were expected to be used. The imaging system 200, 300 compares the number of X-ray emitters 206a-e, 306a-g used to the number of X-ray emitters 206a-e, 306a-g specified by the user input.

When the number of X-ray emitters 206a-e, 306a-g used is less than the number of X-ray emitters 206a-e, 306a-g specified by the user input, the imaging system 200, 300 selects or determines a different X-ray emitter 206a-e, 306a-g from among the one or more X-ray emitters 206a-e, 306a-g (418). The controller 208, 308 may cycle, either sequentially or non-sequentially, through each of the one or more X-ray emitters 206a-e, 306a-g until a threshold number of X-ray emitters 206a-e, 306a-g have been selected to emit a corresponding X-ray beam so that the detector 220, 320 captures or detects the corresponding X-ray image. The threshold number may be equivalent to the number of X-ray emitters 206a-e, 306a-g to be used as indicated in the user input.

When the number of X-ray emitters 206a-e, 306a-g used matches the number of X-ray emitters 206a-e, 306a-g specified by the user input, the imaging system 200, 300 may process the X-ray images (426). The imaging system 200, 300 may reconstruct the tomographic image from the captured images and provide the tomographic image to a user or operator.

The imaging system 200, 300 determines whether another imaging sessions is needed (428). The imaging system 200, 300 may determine whether another imaging session is needed based on the user input. The user input may indicate a number of imaging sessions and/or application. When the there is no other imaging session needed, the imaging system 200, 300 may power down or power off (430). The imaging system 200, 300 may discontinue the delivery of power. Otherwise, the imaging system 200, 300 may reconfigure the controller and/or detector for the next or subsequent imaging system 200, 300 (404).

The implementations of the imaging system 200, 300 may have a similar or like components and/or structure, which may have the same or similar functionality. For example, the computing devices 222, 322, the power sources 202, 302, the user interfaces 224, 324, the X-ray sources 206, 306, the controllers 208, 308 the X-ray emitters 206a-e, 306a-g, and/or the additional filters 226a-e, 326a-b may have the same or similar structure and/or functionality across the different implementations of the imaging systems 200, 300. Other components, such as the step-up transformer 204 may also be interchanged or included in any or all of the different implementations of the imaging system 200, 300 to perform the same or similar functionality, as described above.

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. An imaging system, comprising:
    an X-ray generator configured to provide an alternating current (AC) high voltage output having an amplitude and a frequency;
    a distributed X-ray source coupled to the X-ray generator and including an array of X-ray emitters and configured to generate an X-ray beam with an energy spectrum based on the AC high voltage output; and
    a controller coupled to the X-ray generator and to the distributed X-ray source and configured to:
        control a timing of when to engage an X-ray emitter of the array of X-ray emitters of the distributed X-ray source based on a predefined firing pattern;
        select a voltage level provided to the distributed X-ray source for the X-ray beam based on a predefined pattern of X-ray spectrum;
        engage a first X-ray emitter, of the array of X-ray emitters, at a first time to generate a first X-ray spectrum; and
        engage a second X-ray emitter, of the array of X-ray emitters, at a second time to generate a second X-ray spectrum that is different from the first X-ray spectrum.

2. The imaging system of claim 1, wherein the controller is configured to:
    synchronize the timing of when to engage the X-ray emitter with the AC high voltage output, wherein the timing is adjusted based on an anode-cathode high voltage feedback signal from the distributed X-ray source.

3. The imaging system of claim 2, wherein the timing of when to engage each X-ray emitter of the array of X-ray emitters is different from other X-ray emitters of the array of X-ray emitters and is based on an AC high voltage that may produce a pre-defined X-ray spectrum and on the rate of change of the AC high voltage.

4. The imaging system of claim 1, wherein the imaging system is a tomographic imaging system.

5. The imaging system of claim 1, wherein the AC high voltage output of the X-ray generator is a combination of a direct current (DC) voltage and an AC high voltage.

6. The imaging system of claim 1, further comprising:
    a step-up transformer coupled to the X-ray generator and to the distributed X-ray source, the step-up transformer configured to receive the AC high voltage output as an input and output a second AC voltage that is greater than the input, wherein the AC high voltage output uses an alternating current (AC) power line frequency.

7. The imaging system of claim 1, further comprising:
a plurality of X-ray filters that are configured to receive the X-ray beam with the energy spectrum as produced by the array of X-ray emitters and reduce or eliminate lower energy X-ray photons within the energy spectrum.

8. The imaging system of claim 1, further comprising:
a plurality of X-ray filters that are configured to use K-edge absorption phenomenon for spectrum adjustments.

9. The imaging system of claim 1, further comprising:
a plurality of X-ray filters; and
a second controller that is coupled to the plurality of X-ray filters and configured to mechanically select various combinations of the plurality of X-ray filters.

10. The imaging system of claim 1, further comprising:
a processor configured to generate a three-dimensional (3D) image information or 3D visualization; and
a detector configured to:
  receive an X-ray exposure of the X-ray beam with a first energy spectrum;
  generate a first X-ray image based on the X-ray exposure of the X-ray beam with the first energy spectrum;
  store the first X-ray image;
  receive a second X-ray exposure of the X-ray beam with a second energy spectrum;
  generate a second X-ray image based on the second X-ray exposure of the X-ray beam with the second energy spectrum; and
  store the second X-ray image.

11. The imaging system of claim 10, wherein the processor is configured to capture the X-ray exposure and the second X-ray exposure at a speed that enables real-time three-dimensional (3D) X-ray imaging.

12. The imaging system of claim 1, wherein the array of X-ray emitters are cold cathode X-ray emitters and are designed, arranged, or controlled to facilitate regulatory compliance of a focal spot size in a range of operating high voltages.

13. The imaging system of claim 1, further comprising:
a plurality of X-ray filters with different X-ray filtering characteristics;
wherein the controller is configured to:
  select one or more of the plurality of X-ray filters that results in dual-energy X-ray imaging or multi-energy X-ray imaging for the predefined firing pattern.

14. The imaging system of claim 1, further comprising:
an actuator configured to move or position the distributed X-ray source in three dimensions around an object that is to be imaged to increase tomographic data when capturing image data.

15. A method of performing real-time spectral tomographic reconstruction of an object, comprising:
providing, by an X-ray generator, an alternating current (AC) voltage output to a plurality of X-ray emitters of an X-ray source, wherein the AC voltage output has a waveform with an amplitude and a frequency;
selecting, by a controller, a first X-ray emitter from among the plurality of X-ray emitters of the X-ray source to generate a first X-ray beam with a first energy spectrum based on the AC voltage output;
selecting, by the controller, a second X-ray emitter from among the plurality of X-ray emitters of the X-ray source to generate a second X-ray beam with a second energy spectrum based on the AC voltage output, wherein the first energy spectrum is different from the second energy spectrum as a result of the first X-ray emitter being engaged at a different time than the second X-ray emitter, wherein a plurality of X-ray beams comprises at least the first and second X-ray beams.

16. The method of claim 15, further comprising:
adjusting, using one or more additional X-ray filters, an X-ray beam energy spectrum to produce an energy distribution required by X-ray imaging application.

17. The method of claim 16, further comprising:
detecting, using an X-ray detector, the plurality of X-ray beams created by the X-ray source in rapid succession to form images.

18. The method of claim 17, wherein the plurality of X-ray filters of the X-ray source use K-edge absorption phenomenon for spectrum adjustments.

19. The method of claim 18, further comprising:
processing images from the X-ray detector using 3D reconstruction techniques in real-time; and
providing the reconstructed 3D information to a user.

20. The method of claim 15, further comprising:
synchronizing the X-ray generator and the controller to create an X-ray trigger point on a waveform of the AC voltage output such that the X-ray source is enabled at a time when the AC voltage output generates a desired X-ray output spectrum.

* * * * *